(12) United States Patent
Nordberg et al.

(10) Patent No.: US 10,018,538 B2
(45) Date of Patent: Jul. 10, 2018

(54) APPARATUS FOR SPREADING A FLUID ACROSS A SUBSTRATE AND METHOD OF USING THE SAME

(71) Applicant: RareCyte, Inc., Seattle, WA (US)

(72) Inventors: Joshua Nordberg, Bainbridge Island, WA (US); Daniel Campton, Seattle, WA (US); Steve Quarre, Woodinville, WA (US); David Stewart, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 282 days.

(21) Appl. No.: 14/948,327

(22) Filed: Nov. 22, 2015

(65) Prior Publication Data

US 2016/0076979 A1    Mar. 17, 2016

Related U.S. Application Data

(63) Continuation of application No. 14/801,637, filed on Jul. 16, 2015, now Pat. No. 9,222,857, which is a continuation of application No. 14/465,065, filed on Aug. 21, 2014, now Pat. No. 9,121,798.

(60) Provisional application No. 61/869,881, filed on Aug. 26, 2013.

(51) Int. Cl.
*G01N 3/00* (2006.01)
*G01N 1/28* (2006.01)
*G01N 1/31* (2006.01)
*B01L 3/00* (2006.01)

(52) U.S. Cl.
CPC ............ *G01N 1/2813* (2013.01); *B01L 3/502* (2013.01); *G01N 1/312* (2013.01); *B01L 2200/0605* (2013.01); *B01L 2300/06* (2013.01); *B01L 2300/0809* (2013.01); *B01L 2400/0475* (2013.01)

(58) Field of Classification Search
CPC ...................................................... G01N 21/00
See application file for complete search history.

(56) References Cited

U.S. PATENT DOCUMENTS 4,392,450 A * 7/1983 Prevo .................... G01N 1/2813
118/120
5,676,910 A * 10/1997 Levine ................. G01N 1/2813
118/100

\* cited by examiner

*Primary Examiner* — Jyoti Nagpaul
(74) *Attorney, Agent, or Firm* — Shay Glenn LLP

(57) ABSTRACT

This disclosure is directed to an apparatus and method for spreading a fluid across a substrate. A spreader for spreading a fluid across a substrate includes a wiper and a frame. The wiper and the frame may mate to permit translation of the wiper across, and with respect to, the frame. The wiper spreads the fluid across the substrate and the frame supports the wiper and the substrate. The frame may also include a ramp to cause a portion of the wiper to lift away from the substrate.

11 Claims, 12 Drawing Sheets

APPARATUS FOR SPREADING A FLUID ACROSS A SUBSTRATE AND METHOD OF USING THE SAME

CROSS-REFERENCE TO A RELATED APPLICATION

This application is a continuation of application Ser. No. 14/801,637, filed Jul. 16, 2015, which is a continuation of application Ser. No. 14/465,065, filed Aug. 21, 2014, now issued as U.S. Pat. No. 9,121,798, which claims the benefit of Provisional Application No. 61/869,881, filed Aug. 26, 2013.

TECHNICAL FIELD

This disclosure relates generally to smearing a fluid and, in particular, to spreading a fluid across a substrate.

BACKGROUND

Analysis of a biological sample includes the step of placing the biological sample on a substrate, such as a microscope slide, for examination. Once placed on the substrate, the biological sample may be smeared across the substrate, thereby forming a wider and thinner layer of the biological sample to enable more efficient processing, imaging and examination of components of the biological sample. However, non-uniformity may lead to problems with imaging and examination, thereby leading to errors and incorrect analysis. As a result, practitioners, researchers, and those working with suspensions or solutions continue to seek an apparatus and method for repeatedly and uniformly spreading a biological sample, a solution, or a suspension across a substrate.

DETAILED DESCRIPTION

This disclosure is directed to fluid spreaders and methods for spreading a fluid across a substrate. A spreader includes a wiper and a frame. The wiper and the frame may mate to permit translation of the wiper across, and with respect to, the frame. The wiper spreads the fluid across the substrate and the frame supports the wiper and the substrate. The frame may also include a ramp to cause a portion of the wiper to lift away from the substrate.

Spreader

Figure 1A:
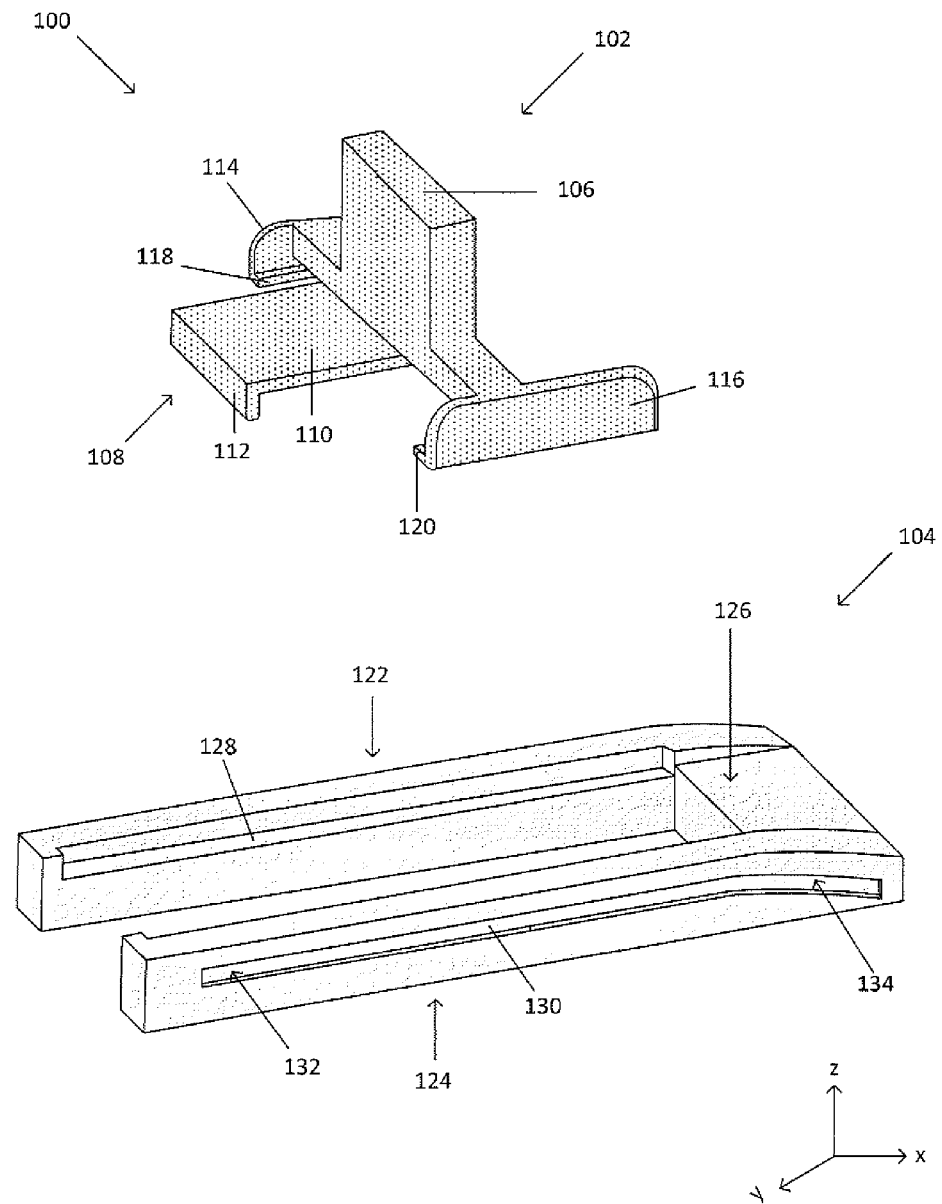
FIG. 1A-1C show an example spreader.

FIG. 1A shows an exploded view of a spreader 100. The spreader 100 includes a wiper 102 and a frame 104. The wiper 102 spreads a fluid across a substrate held in position by the frame 104. The wiper 102 includes a handle 106 that enables a user to move the wiper 102 along the frame 104 while eventually spreading a fluid across the substrate held in place by the frame 104. The wiper 102 also includes a platform 108. The platform 108 includes an extension 110 extending from the handle 106 and a blade 112 extending downward from the extension 110 to engage the fluid. The platform 108 may be sized to contact at least a portion of a surface of the substrate or may be sized so as to not contact the surface of the substrate. The blade 112 may be straight, angled, or curved. The platform 108 may be composed of metal, ceramic, rubber, plastic, or a combination thereof. Alternatively, the extension 110 may be removed, and the blade 112 and the handle 106 may be longitudinally co-axial, thereby sharing the same central axis. Alternatively, the spreader 100 may allow for back and forth spreading, such that the wiper 102 is moved in a first direction and then is moved backwards in a second direction. For example, the blade 112 may include a double plough to spread the suspension in opposite directions.

The wiper 102 also includes a first wing 114 and a second wing 116. The first and second wings 114 and 116 include first and second flanges 118 and 120, respectively. The first and second flanges 114 and 116 are directed inward to mate with a first guide (not shown) and a second guide 118, respectively, located on opposite sides of the frame 104 handle 106 flanges 114 and 116.

The frame 104 includes parallel first and second anus 122 and 124 that extend from a stanchion 126. The first and second arms 122 and 124 each include a shelf 128. The shelf 128 is a cut-out from an inner top portion of the respective side. The shelf 128 supports the substrate when the substrate is inserted into the frame 104. The shelf 128 inhibits translation of the substrate relative to the frame 104. The first and second arms 122 and 124 may be adjustable, thereby allowing for different dimensioned substrates to be used within the same frame 104.

The wiper 102 and the frame 104 may be interlockable via a tongue and groove connection to permit translation of the wiper 102 across, and with respect to, the frame 104. The first and second flanges 118 and 120 of the wiper 102 (i.e. the tongues) mate with a first guide (not shown) and a second guide 130 (i.e. the grooves), respectively. The first guide (not shown) and the second guide 130 include a linear portion 132 and a ramp 134. The linear portion 132 permits the wiper 102 to drag the fluid across the substrate at a consistent height. When the wiper 102 reaches and moves across the ramp 134, the blade 112 is lifted away from the substrate to avoid spreading off of the edges and end of the substrate while also allowing for ease of removal of the substrate from the frame 104. The ramp 134 may be angled or curved. The stanchion 126 may support at least a portion of the wiper 102 when the wiper 102 reaches the end of the ramp 134 in such a manner so as to prevent the blade 112 and/or the extension 110 from touching the stanchion 126 or any other portion of the frame 104. Alternatively, movement of the wiper 102 relative to the frame 104 may be constrained to the x-y plane, such as by a flexure mechanism, motorized actuator, linear or non-linear guides, a rotary mechanism, rack-and-pinion, or the like. Alternatively, the flanges may be located on the frame 104 whereas the guides may be located on the wiper 102.

Figure 1B:
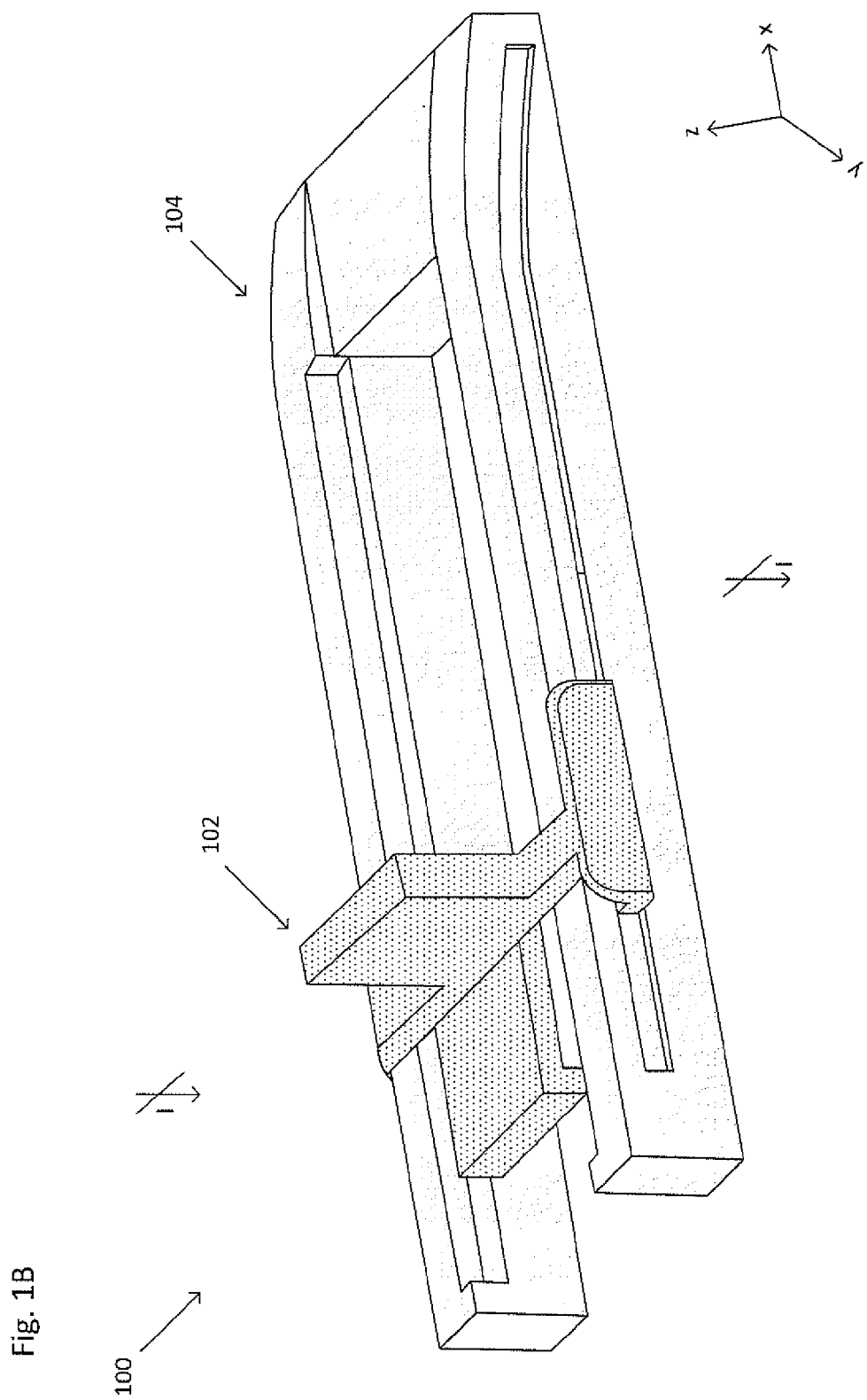
Figure 1C:
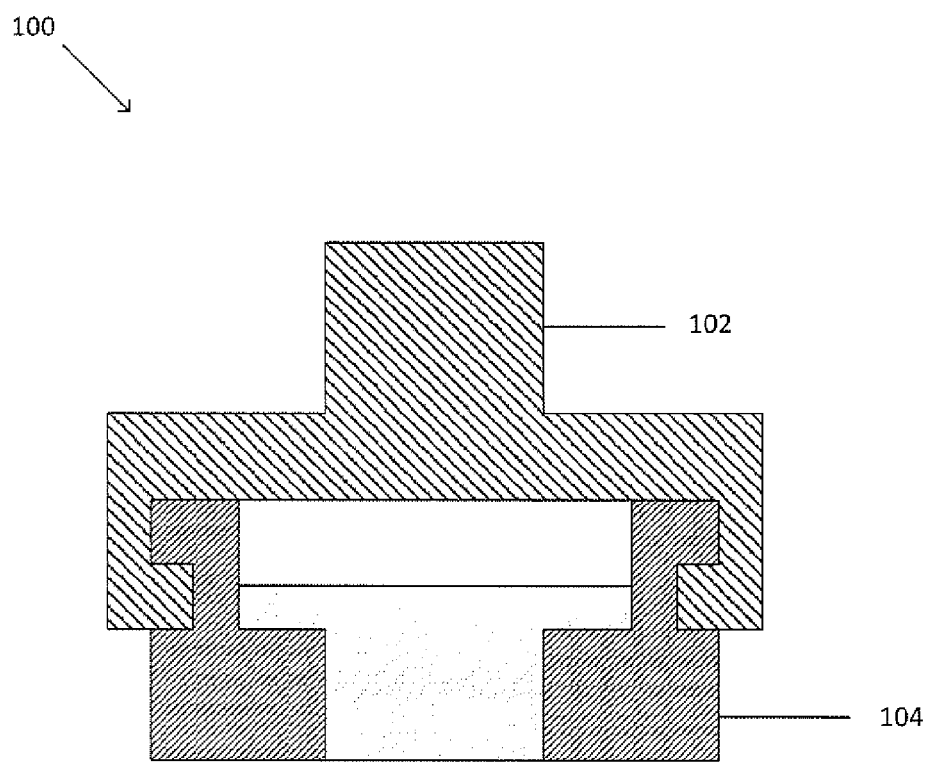
Figure 1C:
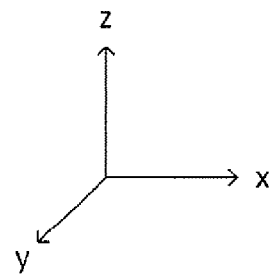

FIG. 1B shows an isometric view of the spreader 100. FIG. 1C shows a cross-section of the spreader 100 taken along the line I-I.

Figure 2A:
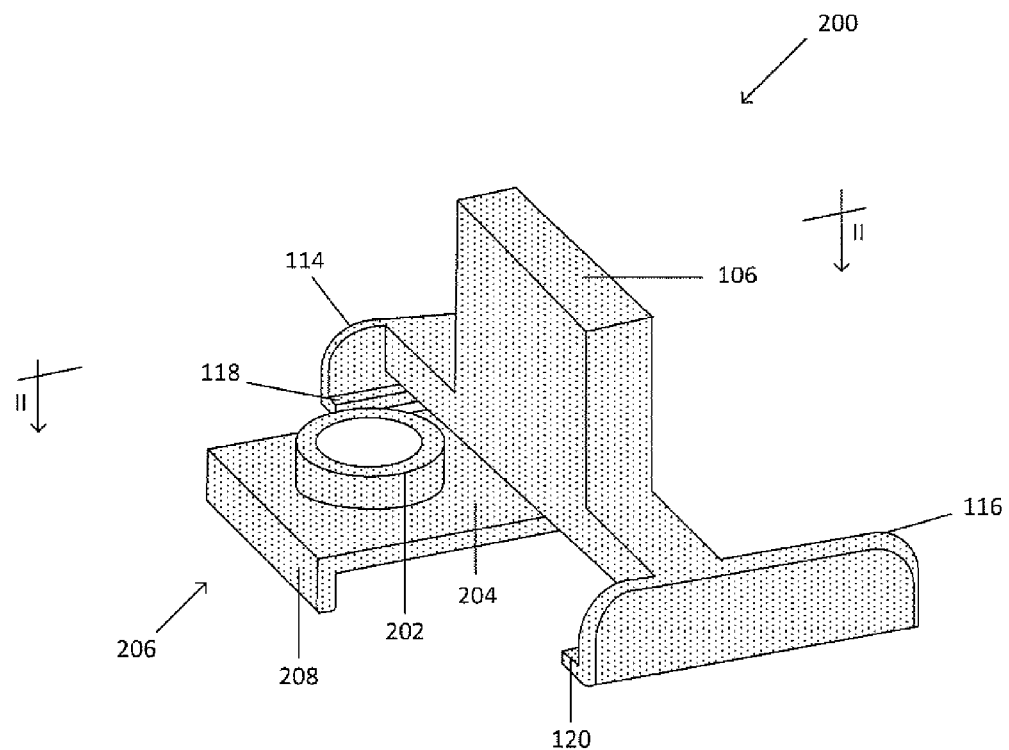
FIGS. 2A-2B show an example a wiper.
Figure 2B:
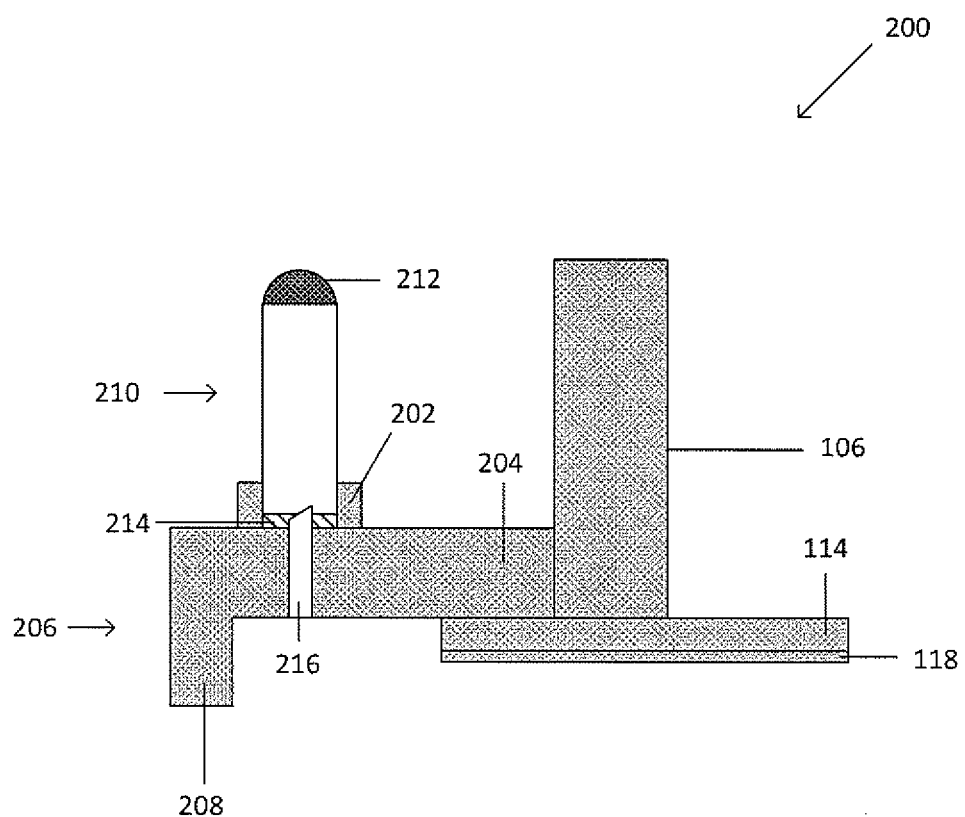

FIG. 2A shows an example of a wiper 200. The wiper 200 is similar to the wiper 102, except that the wiper 200 includes a connector 202. The connector 202 may be located on a extension 204 of a platform 206. The platform 206 also includes a blade 208 similar to the blade 112. The connector 202 permits a vessel (not shown) to dispense a fluid onto the substrate without having to transfer the fluid or portion thereof to the substrate before being inserted into the frame. The connector 202 may be threaded or embedded with a Luer lock. The connector 202 may be any appropriate shape, including, but not limited to cylindrical, rectangular, conical, pyramidal, or the like. The connector 202 may be a hollow receptacle or may be a receptacle with a needle. For example, as seen in FIG. 2B which is a cross-sectional view taken along the line II-II, a tube 210 with a flexible bottom 212 may be inverted such that a cap 214 is punctured by a needle 216. The flexible bottom is pushed, which draws a pre-determined volume of fluid through the needle. The fluid is then dispensed onto the substrate from the needle 216. Alternatively, the fluid may be dispensed via a syringe, a compressible cap, a pump via a fitting, or the like.

Figure 2C:
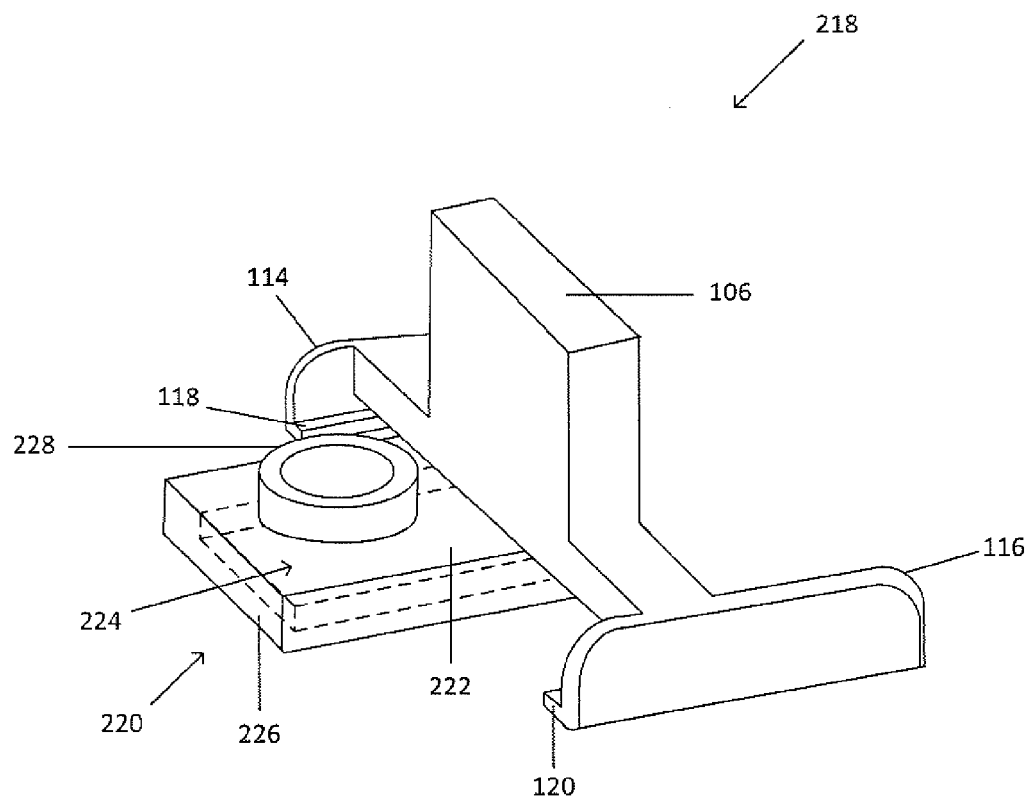
FIG. 2C shows an example wiper.

FIG. 2C shows an example of a wiper 218. The wiper 218 is similar to the wiper 200, except that the wiper 218 includes a platform 220 where the extension 222 is enclosed on the sides to form a cavity 224 on an underside of the platform 220. The extension 222 also includes a blade 226 similar to the blade 112. The extension 222 may also include a connector 228 similar to the connector 202.

Figure 3:
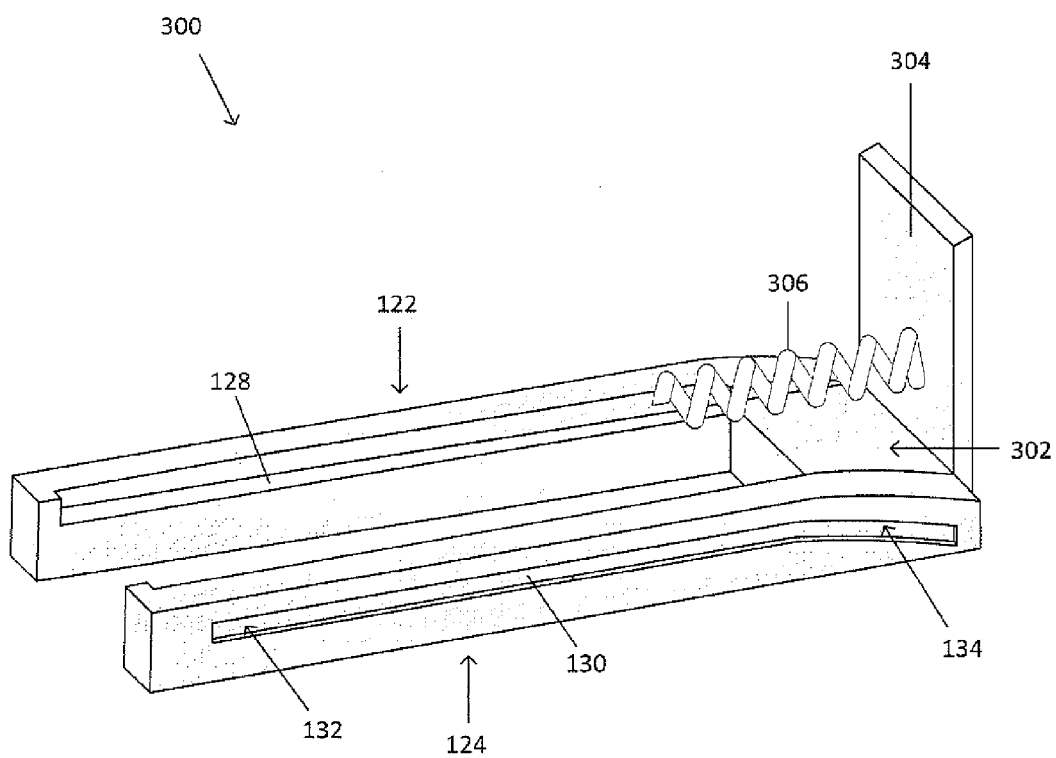
FIG. 3 shows an example frame.
Figure 3:
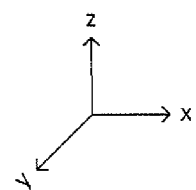

FIG. 3 shows an example of a frame 300. The frame 300 is similar to the frame 104, except that the frame 300 includes a stanchion 302 with a back plate 304. The back plate 304 may include controllable drive mechanism 306 to move the wiper (not shown) along the frame 300 at a constant rate. The controllable drive mechanism 306 includes, but is not limited to, a spring, a damper (e.g. a rotary or linear damper) to move the wiper (not shown) at a constant rate. The controllable drive mechanism 306 may be used to move the wiper (not shown) along the frame at a predictable motion profile as the fluid droplet changes size across the substrate.

Figure 4A:
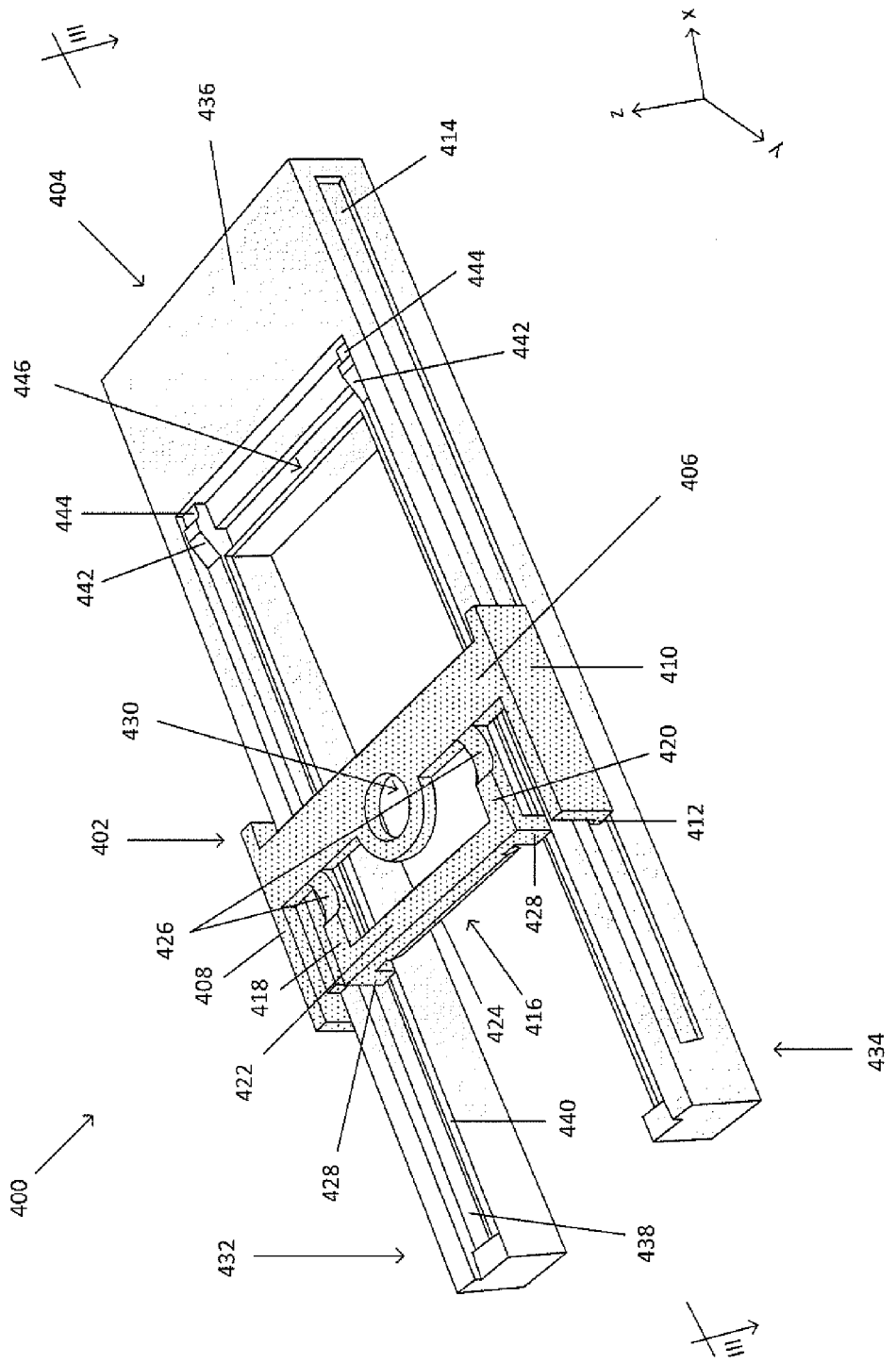
FIGS. 4A-4B show an example spreader.
Figure 4B:
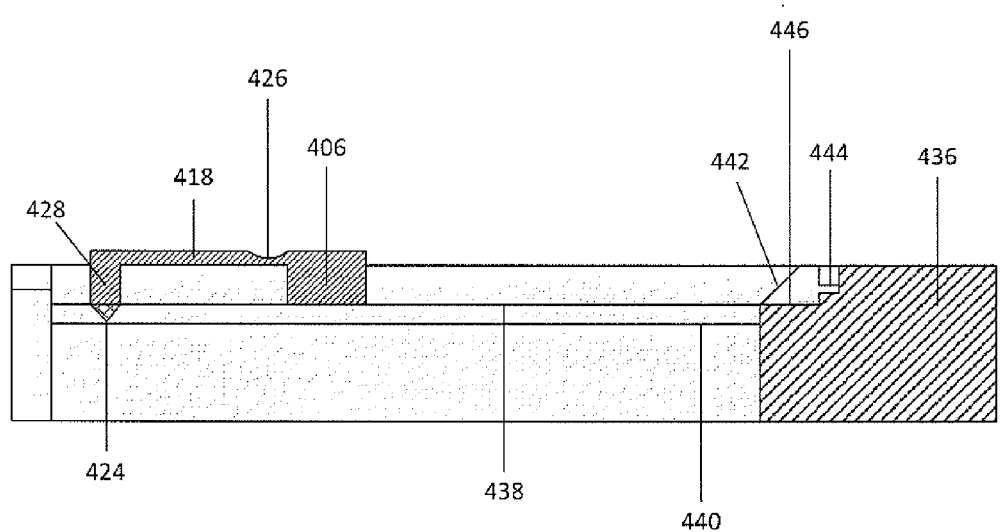
Figure 4B:
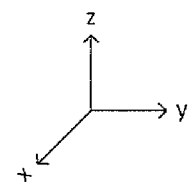

FIG. 4A shows an isometric view of a spreader 400. FIG. 4B shows a cross-sectional view of the spreader 400 taken along the line III-III. The spreader 400 includes a wiper 402 and a frame 404. The wiper 402 includes a main body 406 connected to a first wing 408 and a second wing 410. The first wing 408 includes a first flange (not shown) and the second wing 410 includes a second flange 412. The first flange (not shown) and the second flange 412 mate with a guide 414 of a respective side of the frame 404 (such as by a tongue-and-groove joint) to guide the x-, y-, and z-positions of the wiper 402. The first flange (not shown) and the second flange 412 extend towards the central axis of the main body 404 from the first and second wings 408 and 410, respectively.

The wiper 402 also includes a platform 416. The platform 416 may include first and second support members 418 and 420 extending from and connected to the main body 406. An extension 422 connects the first and second support members 418 and 420 at an end opposite the end at which the first and second support members 418 and 420 connect to the main body 406. The extension 422 includes a blade 424 to interact with a fluid on a substrate, thereby spreading the fluid across the substrate. The blade 424 may be hydrophobic or hydrophilic. The first and second support members 418 and 420 may include flexures 426. The flexures 426 may be cut-outs from the first and second support members 418 and 420 or flexible material to permit flexion of the blade 424 relative to the main body 406. The blade 424 may be sized to contact at least a portion of a surface of the substrate or may be sized so as to not contact the surface of the substrate. The blade 424 may be tapered or flat. The blade 424 may be composed of metal, ceramic, rubber, plastic, or a combination thereof. The wiper 402 also includes feet 428 at the junction of the extension 422 and the first and second support members 418 and 420, respectively, which extend downward and may engage the substrate to maintain a consistent blade height relative to the substrate. The flexures 426 may also be pre-loaded to keep the feet 428 in constant contact with the substrate. Alternatively, the feet 428 may engage a shelf of the frame 404.

The wiper 402 may also include a connector 430. The connector 430 may be located in the main body 406. The connector 430 permits a vessel (not shown) to dispense a fluid onto the substrate without having to transfer the fluid or portion thereof to the substrate before being inserted into the frame. The connector 430 may be a hole, a hollow receptacle, or may be a receptacle with a needle. For example, a tube or tubular main body with a flexible bottom may be inverted such that a cap is punctured by the needle. The flexible bottom is pushed, which draws a pre-determined volume of fluid through the needle. The fluid is then dispensed onto the substrate from the needle. Alternatively, the fluid may be dispensed via a syringe, a compressible cap, a pump via a fitting, or the like.

The connector 430 may be threaded or embedded with a Luer lock. The connector 430 may be any appropriate shape, including, but not limited to cylindrical, rectangular, conical, pyramidal, or the like. The vessel, upon connection with the connector 430, may be used as a handle. Alternatively, the wiper 402 may also include handle to move the wiper 402 relative to the frame 404.

The frame 404 includes a first arm 432 and a second arm 434, the first and second arms 432 and 434 being disconnected at one end and connected at another end via a stanchion 436. The first and second arms 432 and 434 each include a shelf 438. The shelf 438 is a cut-out from an inner top portion of the respective side. A lip 440 is then cut out from the respective shelf 438 within each side. The lip 440 supports the substrate when the substrate is inserted into the frame 404, whereas the shelf 438 supports the feet 428 of the platform 416. The lip 440 inhibits translation of the substrate relative to the frame 404. The first and second arms 432 and 434 may be adjustable, thereby permitting different dimensioned substrates to be used within the same frame 404.

The respective guides 414 are linear. Each shelf 438 also includes a riser 442 that lifts the platform 416 away from the substrate when the wiper 402 reaches the end of the shelf 438. The feet 428 of the platform 416 then rest in a detent 444 located behind each riser 442. A dock 446 supports at least a portion of the wiper 402, such as the blade 424, when the feet 428 reach the detents 444. Alternatively, the guides may be located on the wiper 402 whereas the flanges may be located on the frame 404. The wiper 402 may be moved relative to the frame 404 manually or mechanically by, including, but not limited to, a flexure mechanism, motorized actuator, linear or non-linear guides, a rotary mechanism, or the like.

The frame 404 may also include a back plate. The back plate may include a controllable drive mechanism to move the wiper 402 along the frame 404 at a constant rate. The controllable drive mechanism includes, but is not limited to, a spring, a damper (e.g. a rotary or linear damper) to move the wiper (not shown) at a constant rate. The controllable drive mechanism may be used to move the wiper (not shown) along the frame at a predictable motion profile as the fluid droplet changes size across the substrate.

Figure 5:
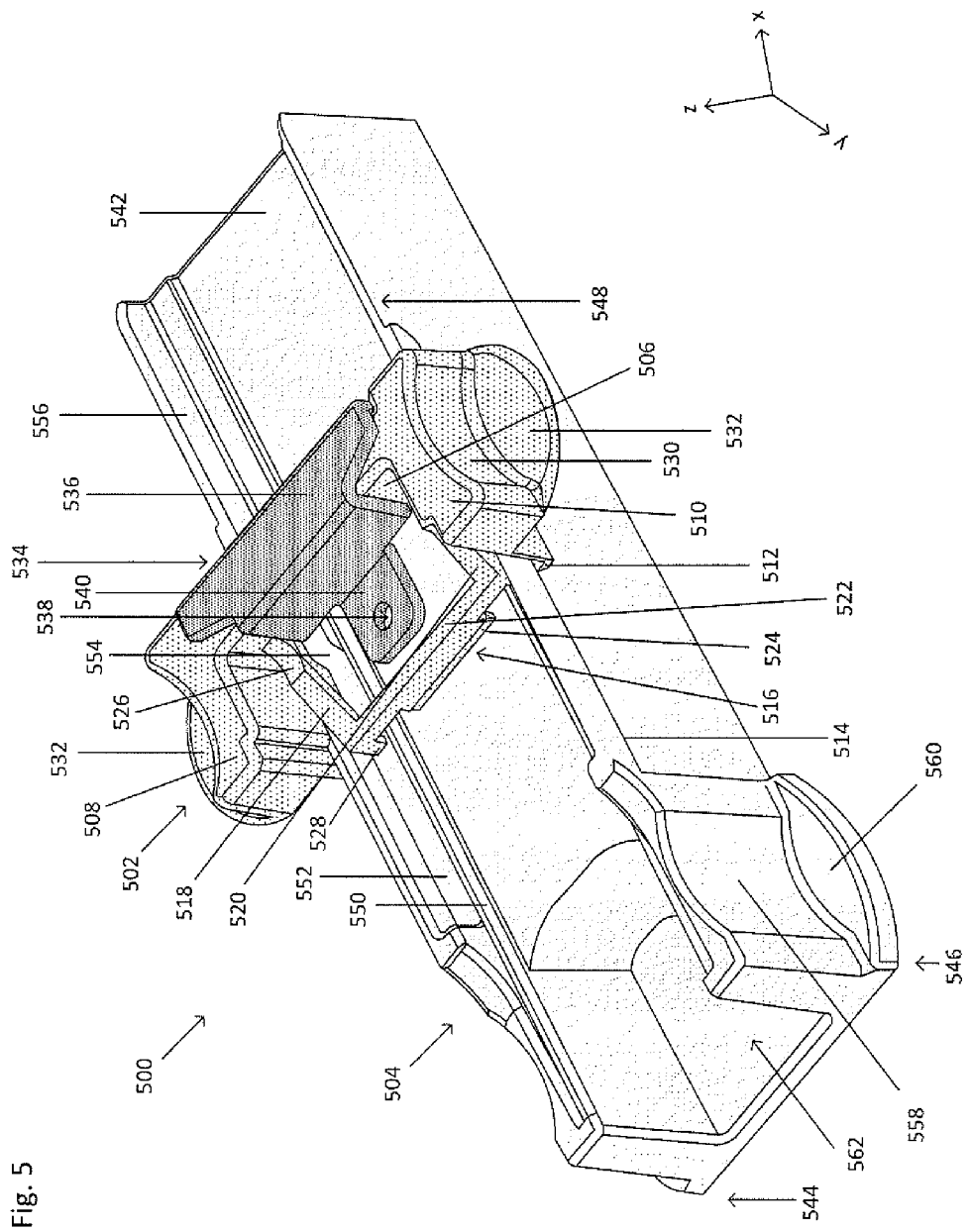
FIG. 5 shows an example spreader.

FIG. 5 shows an isometric view of a spreader 500. The spreader 500 includes a wiper 502 and a frame 504. The wiper 502 includes a main body 506 connected to a first wing 508 and a second wing 510. Each wing 508 and 510 includes a flange 512. The flanges 512 mate with a guide 514 of a respective side of the frame 504 (such as by a tongue-and-groove joint) to guide the x-, y-, and z-positions of the wiper 502. The flanges 512 extend towards the central axis of the main body 504 from the first and second wings 508 and 510, respectively.

The wiper 502 also includes a platform 516. The platform 516 may include first and second support members 518 and 520 extending from and connected to the main body 504. An extension 522 connects the first and second support members 518 and 520 at an end opposite the end at which the first and second support members 518 and 520 connect to the main body 506. The extension 522 includes a blade 524 to interact with a fluid on a substrate, thereby spreading the fluid across the substrate. The blade 524 may be hydrophobic or hydrophilic. The first and second support members 518 and 520 may include flexures 526. The flexures 526 may be cut-outs from the first and second support members 518 and 520 or flexible material to permit flexion of the blade 524 relative to the main body 506. The blade 524 may be sized to contact at least a portion of a surface of the substrate or may be sized so as to not contact the surface of the substrate. The blade 524 may be metal, ceramic, rubber, plastic, or a combination thereof. The blade 524 may be tapered or flat. The wiper 502 also includes feet 528 at the junction of the extension 522 and the first and second support members 518 and 520, respectively, which extend downward and may engage the substrate to maintain a consistent blade height relative to the substrate. The flexures 526 may also be pre-loaded to keep the feet 528 in constant contact with the substrate. Alternatively, the feet 528 may engage a shelf of the frame 504 track 548 The first and second wings 508 and 510 may include a cut-out 530 to permit an operator or another device to grip the wiper 502 to be dragged across the frame 504. The first and second wings 508 and 510 may also include a guard 532 to prevent the operator or another device from disturbing other samples when at least two frames are placed side-by-side. The guard 532 may also permit for consistent grip height from wiper to wiper and when the wiper is moved from frame to frame.

The wiper 502 may also include a connector 534. The connector 534 may be a separate piece from the wiper 502 and may attach to the main body 506 of the wiper 502 via an attachment segment 536. The attachment segment 536 may be a clip so as to slip onto the main body 506. The connector 534 permits a vessel (not shown) to dispense a fluid onto the substrate without having to transfer the fluid or portion thereof to the substrate before being inserted into the frame. The connector 534 may include a bore 538 within a pedestal 540 extending from the attachment segment 536 towards the blade 542 of the wiper 502. The bore 538 may accept or mate with the vessel and may be threaded or may include a Luer lock. Alternatively, the bore 538 may include a needle to puncture the vessel. For example, a tube or tubular main body with a flexible bottom may be inverted such that a cap is punctured by the needle. The flexible bottom is pushed, which draws a pre-determined volume of fluid through the needle. The fluid is then dispensed onto the substrate from the needle. Alternatively, the fluid may be dispensed via a syringe, a compressible cap, a pump via a fitting, or the like.

The frame 502 includes a stanchion 542 which adjoins first and second sides 544 and 546. Each side of the frame 502 includes the guide 514, which may extend the full length of the respective side or may extend only a portion of the respective side. When the guide 514 only extends a portion of the respective side, the guide 514 may include a notch 548 to permit insertion of the wiper 502 onto the guide 514. The track 548 may be angled to maintain a relative distance of the blade 524 to the sample based on the changing volume of the not-yet-smeared portion of the sample (i.e. to maintain a consistent blade 524 to smear area ratio). Each flange 512 may be passed through the respective notch 548 and then moved to engage the respective guide 514. Each side also includes a shelf 550 to support the substrate when the substrate is inserted into the frame 504 and a mantle 552 to support and engage the feet 528 of the wiper 502. The mantle 552 may include a riser 554 to lift the blade 524 of the wiper 502 away from the substrate. The frame 504 may also include a lip 556 to inhibit translation of the substrate relative to the frame 504. Each side of the frame 504 may include a cut-out 558 to permit an operator or another device to grip the frame 504 while the wiper 502 is dragged across the frame 504. Each side of the frame 504 may also include a base 560 so that the operator or another device may stabilize the frame 504 by exerting a force on the frame 504. The frame 504 may also include a cavity 562 to permit the substrate to be inserted and removed from the frame 504 without touching the portion of the substrate that has or may receive the sample. The frame 504 may be level or angled (i.e. approximately 0.1°-5°).

The frame 504 may also include a back plate. The back plate may include controllable drive mechanism (not shown) to move the wiper 502 along the frame 504 at a constant rate. The controllable drive mechanism (not shown) includes, but is not limited to, a spring, a damper (e.g. a rotary or linear damper) to move the wiper (not shown) at a constant rate. The controllable drive mechanism (not shown) may be used to move the wiper (not shown) along the frame at a predictable motion profile as the fluid droplet changes size across the substrate.

Figure 6:
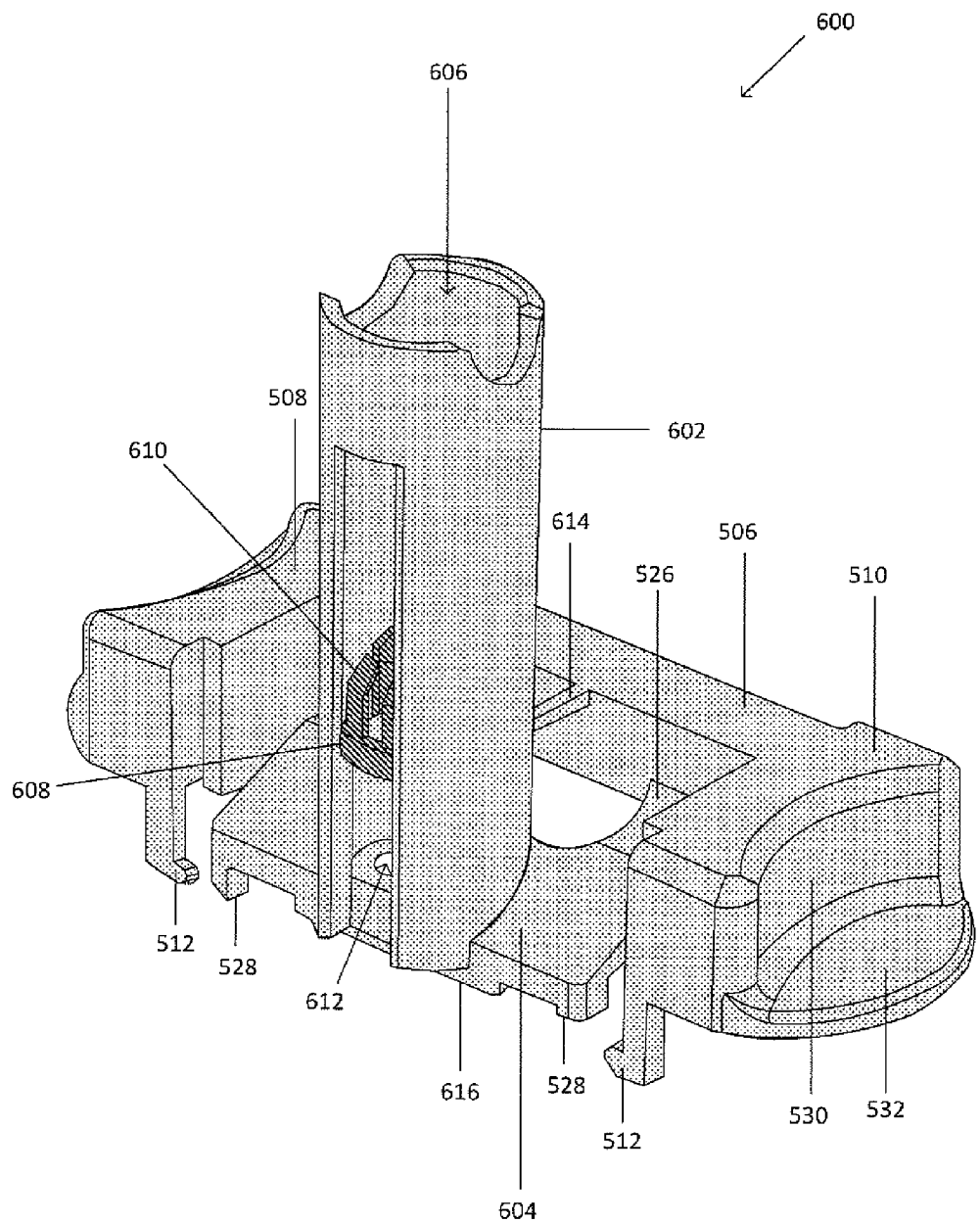
FIG. 6 shows an example wiper.

FIG. 6 shows an isometric view of a wiper 600. The wiper 600 is similar to the wiper 502 except the wiper 600 includes a receptacle 602 extending from a brace 604. The receptacle 602 includes a bore 606 that spans the length of the receptacle and is configured to receive a vessel. The receptacle 602 may also include a collar 608, which may include fingers 610, to secure the vessel within the receptacle 602. The receptacle 602 holds the vessel containing a sample to be dispensed through an aperture 612. Alternatively, the receptacle 602 may include a needle to be inserted into the vessel to draw a portion of the sample out and onto the substrate. The needle extends vertically, thereby being parallel with the wall of the receptacle 602.

The wiper 600 may also include an abutment 614 that extends between the main body 506 and the receptacle 602 to support the receptacle 602. The brace 604 may be connected to the main body 506 via the flexures 526. The brace 604 includes a blade 616 similar to the blade 524.

The wiper may be composed of a variety of different materials including, but not limited to, a ceramic; metals; organic or inorganic materials; and plastic materials; and combinations thereof. The wiper may be disposable or re-useable. The frame may be composed of a variety of different materials including, but not limited to, a ceramic; metals; organic or inorganic materials; and plastic materials; and combinations thereof. The frame may be disposable or re-useable. The tracks may be on the outer side of the respective first and second sides or may be on the inner side of the respective first and second sides.

Alternatively, the spreader may include multiple frames lined up next to one another. A wiper may include multiple blades, such that the number of blades is equal to the number of frames. The blades may share a handle such that pulling on the handle causes all of the blades to move simultaneously. The blades may also share first and second arms so as to move off the substrates in unison.

Alternatively, the spreader may be housed in a cartridge to be inserted into a machine and then ejected from the machine after use. A lid of the cartridge may be removable to access the contents or a handle and connector may extend through the lid, so as to dispense the fluid onto the substrate and the move wiper to spread the fluid.

Method

For the sake of convenience, the methods are described with reference to an example fluid of buffy coat. But the methods described below are not intended to be so limited in their scope of application. The methods, in practice, may be used with any kind of suspension, solution, or fluid. For example, a sample fluid may be urine, blood, Buffy coat, red blood cells, plasma, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. The method and apparatus may also be used with another appropriate solution or suspension. Furthermore, the example fluids may be mixed with a processing solution, such as a preservative, a cell adhesion solution, a fixative, or the like, from previous processing or for subsequent processing and analysis.

Figure 7:
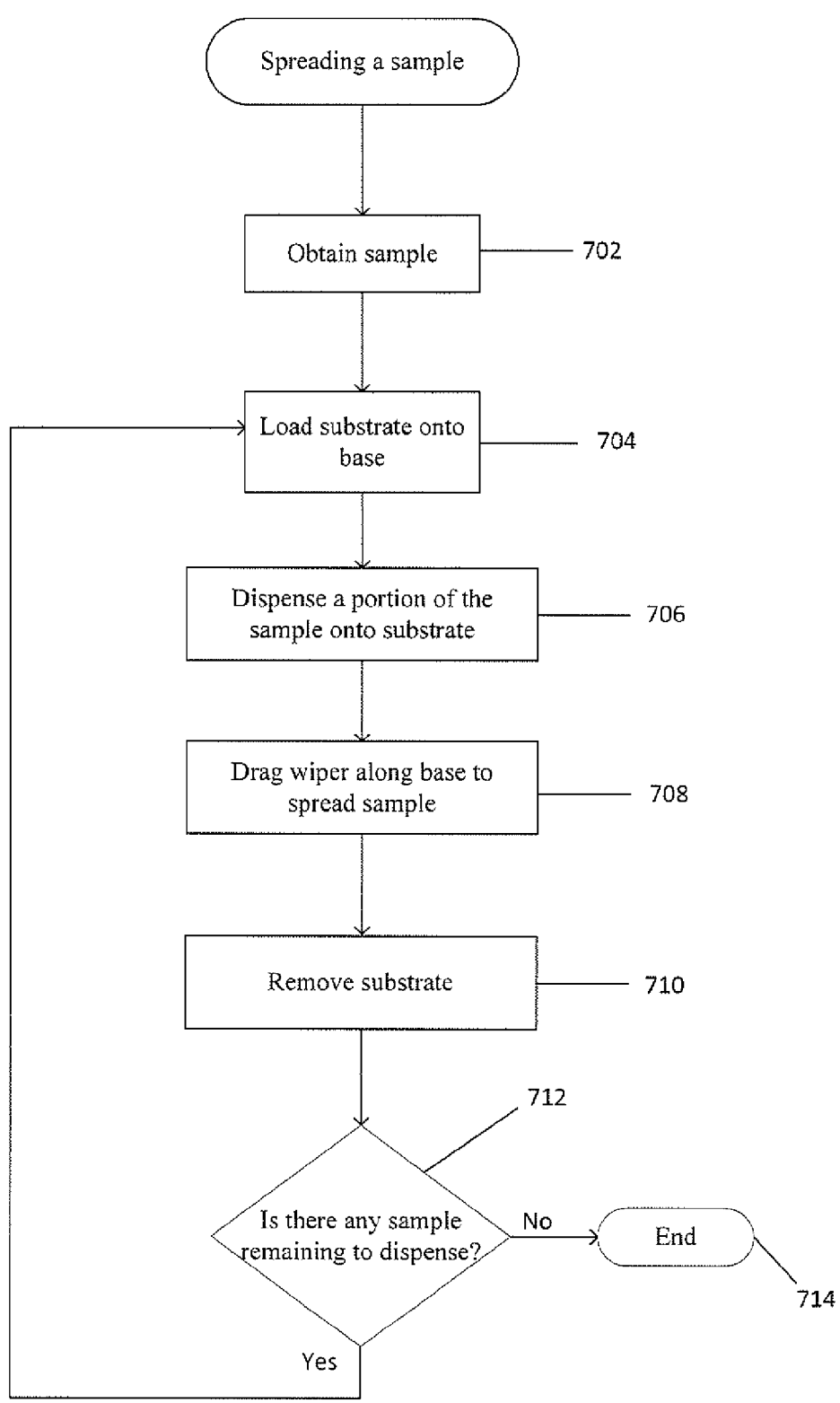
FIG. 7 shows a flow diagram for spreading a sample with a spreader.

FIG. 7 shows a flow diagram for spreading a sample with a spreader. In block 702, a sample of buffy coat may be obtained, such enrichment and/or isolation, and held within a vessel. In block 704, a substrate, such as a microscope slide, may be pre-loaded onto a shelf of a frame. In block 706, at least a portion of the buffy coat sample may be dispensed onto the substrate. The buffy coat may be dispensed in one drop or in more than one drop on the substrate. When one drop is dispensed onto the substrate, the drop may be approximately equidistant between the long sides of the substrate. When more than one drop is dispensed onto the substrate, the drops may be equally spaced apart between the long sides of the substrate.

In block 708, a wiper may be dragged across a frame to spread the sample on the substrate. The protrusion interacts with the buffy coat, thereby wicking the buffy coat outwards (i.e. width) and/or across (i.e. length) the microscope slide. When guides of the wiper slide up a ramp within a track of the frame, the protrusion is lifted away from the microscope slide. In block 710, the substrate may then be removed from the shelf either horizontally or vertically, so as to inhibit any run-off or movement of the huffy coat from the substrate.

In diamond 712, a determination may be made as to whether or not any sample remains in the vessel to be distributed. In oval 714, when no huffy coat remains, the process ends. However, when buffy coat remains, the process continues, starting at block 704 and a new substrate is placed onto the shelf, the wiper is reset, and the process is repeated as many times necessary until the vessel is empty.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A system comprising:
   at least one frame comprising a first guide on a first side and a second guide on a second side; and
   a wiper comprising
      a main body,
      a platform comprising a blade extending at least partially downwardly to engage a fluid on a substrate,
      a first flange on a first side to engage the first guide, and
      a second flange on a second side to engage the second guide,
      wherein the platform extends outwardly from the main body, and
      wherein the platform is flexibly attached to the main body.

2. The system of claim 1, further comprising the substrate.

3. The system of claim 2, the at least one frame further comprising a shelf to the support the substrate.

4. The system of claim 2, the platform further comprising at least two feet extending downwardly and contacting the substrate.

5. The system of claim 1, the at least one frame further comprising a first mantle on the first side and a second mantle on the second side.

6. The system of claim 5, the platform further comprising at least two feet extending downwardly, wherein each foot contacts the mantle on the respective side of the frame.

7. The system of claim 1, wherein the platform is flexibly attached to the main body via flexures.

8. The system of claim 7, wherein the flexures are cut-outs or flexible material.

9. The system of claim 1, wherein the wiper is removably attached to the at least one frame.

10. The system of claim 1, wherein the blade is straight, angled, or curved.

11. The system of claim 1, wherein the blade is rubber, plastic, ceramic, metal, or combinations thereof.

* * * * *